United States Patent

Marro et al.

[11] Patent Number: 6,128,521

[45] Date of Patent: Oct. 3, 2000

[54] SELF ADJUSTING HEADGEAR APPLIANCE USING RESERVOIR ELECTRODES

[75] Inventors: Dominic P. Marro, North Andover; Thomas T. Washburn, Concord; Denis E. LaBombard, Georgetown, all of Mass.

[73] Assignee: Physiometrix, Inc., N. Billerica, Mass.

[21] Appl. No.: 09/113,946

[22] Filed: Jul. 10, 1998

[51] Int. Cl.[7] ................................................. A61B 5/0478

[52] U.S. Cl. ........................ 600/383; 600/391; 600/392; 600/393

[58] Field of Search ........................... 600/383, 391–393; 607/139

[56] References Cited

U.S. PATENT DOCUMENTS

| | | | |
|---|---|---|---|
| 2,426,958 | 9/1947 | Ulett et al. ................................. | 600/393 |
| 3,998,213 | 12/1976 | Price ........................................ | 600/383 |
| 4,770,180 | 9/1988 | Schmidt et al. .......................... | 600/383 |
| 4,928,696 | 5/1990 | Henderson et al. ..................... | 600/383 |
| 5,293,867 | 3/1994 | Oommen ................................. | 600/383 |
| 5,341,806 | 8/1994 | Gadsby et al. .......................... | 600/393 |

*Primary Examiner*—Lee Cohen
*Attorney, Agent, or Firm*—Williams & Associates; Frederick C. Williams

[57] ABSTRACT

This invention defines a system for monitoring the brain activity of a human patient in order to monitor a patient's brain electrical activity. The system uses a plurality of receptors which are mounted in predetermined anatomical positions on the patient's head. The receptors are secured by adhesive foam patches. The appliance fits snugly to the head with the aid of self-adjusting strap that carry imbedded electrical circuitry for the receptors. Electrical connectivity in locations where scalp hair is most likely to be present is improved by the use of braille-tip electrodes fitted with large gel reservoirs.

15 Claims, 4 Drawing Sheets

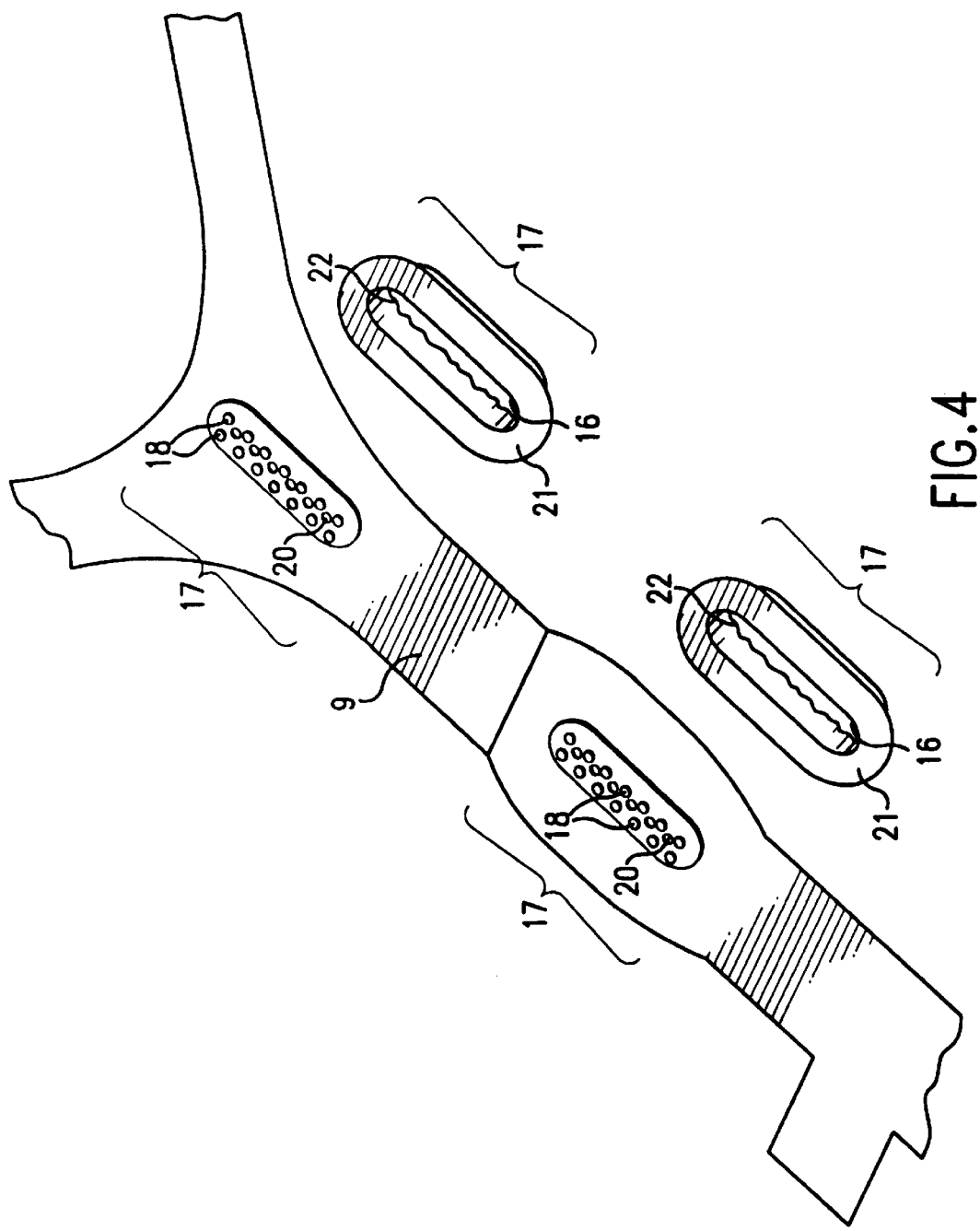

SELF ADJUSTING HEADGEAR APPLIANCE USING RESERVOIR ELECTRODES

FIELD OF THE INVENTION

This invention relates to a seven-receptor monitoring appliance for collecting electroencephalographic data from a human brain. The appliance is designed to be used in conjunction with apparatus monitor a patient's level of consciousness but may be usable for other monitoring applications which collect electroencephalograph (EEG) signals.

BACKGROUND OF THE INVENTION

A common means of monitoring electrical activity of body functions in humans is via receptors, such as electrodes, applied to the patient's skin. Monitoring brain activity, in particular, typically requires a plurality of electrically-connected receptors to be applied to predetermined, anatomically-precise sites on the patient's head.

Where the goal of monitoring electrical activity in the brain is to provide access to the particular recording sites that provide the best determination of anesthesia under a broad range of surgical anesthetics, a number of challenges are presented. First, the proper placement of receptors for electrical signals is essential to registering electrical activity in a fashion that can be interpreted medically. Second, the receptors must be able to maintain electrical contract with the skin throughout a possibly prolonged monitoring cycle without undue intervention by the clinician or anesthesiologist. In particular, during a surgical procedure the patient may have to be monitored for eight or occasionally ten hours. Maintaining proper impedance at the interface between the receptor and the skin is also very important in assuring readable and interpretable signals. Third, integrity of the sensitive conductors in the appliance must be ensured during hook-up and monitoring. If the conductors become shorted during set up or damaged while in place, the efficacy of the monitoring process may be compromised.

Heretofore, a large number of electrodes have been used to record electrical activity of the human brain. Typical monitoring activities have employed 21 electrodes mounted on the patient's head according to specific systems, primarily the International 10-20 system. It is known to employ electrodes in sets of 21, as for example in U.S. Pat. No. 5,497,934.

For certain applications, however, it is natural to conjecture that such a large number of electrodes might be unnecessary. Indeed, where the purpose of monitoring patient brain activity is to trace the level of consciousness in a patient receiving general anesthetic and thereby control the amount of anesthetic being administered, receptors that are not absolutely necessary for performing the desired patient monitoring function may become a distinct liability.

For example, the greater the number of receptors that are employed, the longer the task of preparing the patient. Where receptors are placed individually, the added set-up time is most pronounced. Placing individual electrodes one-by-one is a tedious process that involves measuring the location of the precise site for attaching each individual electrode, marking the location on the patient's head, preparing each attachment site, attaching the electrode, and wiring the electrode to the monitoring console. Electrode mounting sites are marked on the head of the patient with reference to the nasion, inion, and preauricular points. Marking the 21 standard mounting sites takes about 10 or 20 minutes using a tape measure and grease pencil. The sites are then cleaned with a cotton swab and treated with ground pumice stone or some other abrasive to provide good electrical contact to a conducting filler in a gold- or silver-plated cup electrode. Each electrode is attached individually to the patient's head using tape or collodion which solidifies as it dries and retains the electrode in the desired position on the head. This procedure for attaching 21 electrodes typically requires between 30 and 45 minutes. Then, since each electrode is attached and wired separately, a collection of 6 to 10 foot long wires radiate from the patient's head. These wires have to be individually connected to the console of the monitoring machine.

To a certain extent, the process of mounting 21 electrodes has been shortened by the introduction of devices to mark the scalp and to position electrodes on the patient's head. For example, U.S. Pat. No. 5,293,867 discloses headgear for marking the locations where electrodes are to be sited. Although this shortens the time required for the marking operation, it does not simplify any other aspects of the task—the patient's skin still has to be prepared at each of the 21 sites, and each of the 21 electrodes still must be mounted individually.

The greater the number of receptors, the greater the chance that one or more receptors will be improperly sited or improperly wired during set up. When a traditional approach is used, there is always the risk that the clinician will improperly locate one or more receptor sites.

Use of headgear does not entirely resolve these problems. For instance, U.S. Pat. No. 5,497,934 discloses an elaborate headgear design incorporating a large number of electrodes. While the device assists the clinician in reducing the time for placing and attaching the electrodes, headgear incorporating so many electrodes may have drawbacks associated with maintaining correct placement of all electrodes simultaneously. Since all of the electrodes are interconnected with elastic, moving one electrode may also move a plurality of adjacent electrodes, making it difficult to situate all of the required electrodes simultaneously.

Moreover, headgear such as that disclosed in U.S. Pat. No. 5,497,934 does not resolve the problems of maintaining good surface contact with the patient's skin. The task of preparing by hand the mounting sites for all 21 electrodes may be greatly complicated by the appliance's crisscrossing elastic strips.

A further problem with the headgear such as that disclosed in U.S. Pat. No. 5,497,934 is the possibility that wires can become shorted or improperly connected during set-up. Connectors for the electrodes are typically not integral to the headpiece, because the fixed length of a metallic wire or ribbon is not compatible with the requirement that the appliance contain elastic that stretches to fit the patient's head. The connectors are therefore separate from the headpiece, increasing the appliance's bulk and awkwardness. The appliance does not sit flat against the patient's head, increasing the potential that the headgear will interfere with activities occurring during the surgical procedure and increasing the possibility that the electrodes will become dislodged.

To resolve the problem of improper connection, headgear such as that disclosed in U.S. Pat. No. 5,497,934 usually envision that electrode leads will be bundled into a patient interface cable. The large number of electrodes make the resulting patient interface cable a 10 relatively stiff and cumbersome bundle of 21 6- to 10-foot long wires. A wiring cable of these proportions reduces flexibility in situating the console relative to the patient.

Moreover, the greater the number of receptors, the greater the likelihood that one or more receptors will become dislodged during monitoring. If the patient's head is moved or the patient interface cable is bumped, the conductors pull at and tend to dislodge the electrodes. The risk of a receptor becoming dislodged during an operation is particularly high when the patient is subject to intubation, as intubation can cause extensive movement of the patient's head. At times, the adhesive used to attach the electrodes is not strong enough to maintain both the proper electrical connection and the proper positioning throughout the monitoring session. Furthermore, even receptors that remain attached sometimes fail to make sufficiently good electrical contact with the skin to produce an effective signal. Movement in the cable may also shift the headgear and thereby dislodge the electrodes.

From the patient's perspective, headgear that uses an excessive number of receptors or employs suboptimal adhesion or conductive technology may aggravate the adverse perception of a medical situation. The set-up procedure can be long, tedious and complex which increases anxiety of the patient—particularly a patient that is being prepared for surgery. Clean up is also more complicated when a large number of receptors are used. The patient may have been marked with a grease pencil in multiple locations. Conductive gels used to enhance the electrical connection may be spread all over the patient's scalp.

Another obvious shortcoming associated with a large number of receptors is the expense. When the headgear utilizes 21 electrodes and contains the associated connectors, it becomes a fairly complex and costly device. Accordingly, it is common to retain headgear for use on multiple patients while replacing the electrodes with each use. The drawbacks of reuse are particularly acute in the environment of an operating room where cleanliness is an issue. The process of cleaning or sterilizing the headgear could compromise some of the initial properties of the materials, for example, elastic will tend to lose its elasticity when heated or subjected to particular chemicals. If the elasticity of the headgear is affected by age or cleaning (particularly where the loss of elasticity is not uniform in all sections of the headgear), then the headgear will lose its ability to position the electrodes correctly and to exert adequate force to maintain the desired electrical contact during monitoring. It would be ideal if the headgear was so inexpensive as to be disposable.

It has been suggested that headgear designed to accept a large number of electrodes could be utilized with a lesser number of electrodes and would provide a level of service equivalent or similar to an appliance designed specifically for a reduced number of electrodes. Regardless of the number of electrodes mounted in a headpiece designed for a large number of electrodes, such as that disclosed in U.S. Pat. No. 5,497,934, the task of siting electrodes properly on the patient's head could be adversely affected by the many crisscrossing elastic strips that transmit movement and force from one section of the headpiece to another. The difficulties with accommodating hair on a patient would be exacerbated by such a close network of elastic strips. Furthermore, headgear designed to accept a large number of electrodes would in all likelihood remain wired for its full complement of electrodes. For these and other reasons, utilizing headgear designed for a large number of electrodes to monitor activity using a lesser number of electrodes is undesirable.

Accordingly, an object of this invention is to provide an appliance that uses a minimal number of receptors to monitor the brain activity of a human patient for the purpose of ascertaining the level of consciousness of the patient. Another object of this invention is to provide a convenient means of connecting the monitoring appliance to a console that will interpret the information being monitored with minimal interference with medical procedures and minimal safety risks. A further object of this invention is to provide a means whereby the clinician or anesthesiologist is able to quickly locate and prepare the exact sites where each of the receptors must be attached to the patient's head in order to be medically effective during monitoring without the necessity to first place then remove the appliance from the patient's head before preparing the skin surface or the necessity to work around tightly crisscrossed elastic strips. Another object of this invention is to provide a means of securing the receptors that adjusts easily to the human head in a wide variety of shapes and sizes. Another object of this invention is to avoid the use of glue or paste to secure the appliance on the patient's head. An additional object of this invention is to provide an appliance that is secure enough to stay reliably attached during typical surgeries, and procedures such as intubation. Accordingly, an object of this invention is to provide a means of securing the receptors to the patient's head that will withstand significant movement of the head at any time during the monitoring session without dislodging any receptor or interrupting gathering of the electrical signals by the receptors. Another object of this invention is to provide an appliance where the electrical circuitry for the receptors is integral to headpiece. A further object of this invention is to provide an appliance which is inexpensive to manufacture and which can be used as a medical disposable. An additional object of this invention is to provide an appliance that requires no preparation of the skin surface at mounting sites including those sites where scalp hair is present.

SUMMARY OF THE INVENTION

Recent analysis of EEG signals has established that much of the information from the 21 cranial positions identified in the International 10-20 system or even from a smaller number of positions is cumulative or redundant. Further analysis of a significant database of EEG signals has shown that the signals from as few as seven receptors or electrodes can provide the information necessary for transforming the received EEG signals into measures of awareness sufficient for monitoring of anesthesia. It also appears possible that five receptors give enough information. It has also been determined which subset or subsets of the 21 International 10-20 positions give the best quality and compilation of independent information sufficient for anesthesia monitoring.

Accordingly, this invention defines a disposable, self prepping, head-mounted appliance yielding reliable access to a small number of particular electroencephalographic (EEG) recording sites that provide the best determination of patient anesthesia under a broad range of surgical anesthetics. The invention monitors brain activity to a degree sufficient for ascertaining the level of consciousness of the patient. In essence, the receptor array disclosed monitors sites that factor significantly into the determination of patient level of consciousness.

Most generally, the invention is an appliance for collecting EEG signals from a patient's head, which includes a flexible strap consisting of an anterior segment which longitudinally traverses the crown of said patient's head and a plurality of posterior branch segments; each posterior branch segment projects from the posterior end of the anterior segment at an angle to the center line of the anterior segment and traversing therefrom portions of the rear of the patient's head, and each of the plurality of posterior branch segments incorporating a means for adjustment of length of said posterior branch segment. Each of the plurality of posterior branch segments extends from the posterior end of said anterior segment to an adhesive patch on which at least one receptor is mounted. Two of the plurality of posterior branch segments are disposed symmetrically on either side of patient's head so as to comprise two mastoid segments. Each of the mastoid segments is placed in a predetermined anatomical position behind each of the patient's ears in the mastoid region and is comprised fo at least one receptor. At the anterior end of said anterior segment, a frontal adhesive patch in which is mounted at least one receptor is situated so that the at least one receptor may be placed in at least one predetermined anatomical position on the forehead of said patient. In the central and posterior portions of the anterior segment, at least one crown receptor is mounted so that it may be placed in at least one predetermined anatomical position on the crown of the patient's head. A connector tab extends from said anterior segment to a connector; and includes electrical conductors contained in said strap so as to connect electrically each of the at least one receptor in the frontal adhesive patch, at least one crown receptor, each of the mastoid receptors, and any other receptors with a corresponding contact in the connector so that independent signals may be transmitted from each receptor out of the appliance to external devices.

Alternatively, the invention is an appliance for mounting on the head of a patient for collecting electroencephalographic signals, comprising a frontal adhesive patch securing a plurality of receptors situated in predetermined anatomical positions on the forehead of said patient. A central strap extends from said frontal adhesive patch on said forehead and longitudinally traversing the crown of the patient's head, said central strap incorporating a means for adjustment of length and incorporating a plurality of receptors mounted in predetermined anatomical positions. A circumferential band passes about the patient's head above the patient's ears and attached to said frontal adhesive patch. Two mastoid straps extend downward from said circumferential band to two mastoid adhesive patches, each mastoid adhesive patch securing a receptor mounted in a predetermined anatomical position, one of said mastoid adhesive patches being located in a predetermined anatomical position behind the left ear of the patient and the other of said mastoid adhesive patches located in a predetermined anatomical position behind the right ear of the patient, and may also include additional receptors for attachment to patient's ears. Said plurality of receptors mounted in predetermined anatomical positions comprise three frontal receptors, two central receptors, and two mastoid receptors.

Important features of this invention include a roll up length adjuster for a strap carrying electrical conductors for medical application, said adjuster comprised of self-adjusting elastic coils formed from a portion of said strap. Another version of that feature is a roll up length adjuster for a strap carrying electrical conductors for medical application, said adjuster comprising a rollup clip comprised of a portion of said strap wrapped around a spring-loaded central hub in such a way that the tension exerted by said spring-loaded central hub causes a portion of said segment to roll up upon itself and such that the portion of said segment not rolled up lies flat against the patient's head.

Another important feature of this invention is a novel receptor for collecting electroencephalographic signals comprised of a typically hemispherical reservoir with pressure openable partially slit or perforated flat surfaces on the side of the appliance adjacent to the patient's head which contains electrolytic gel. The reservoir is pressed to deploy the electrolytic gel. Another receptor surface enhancement embodiment is a receptor including Braille tip electrodes having protuberances molded into -an embossed receptor on the side of the appliance adjacent to the patient's head.

An objective of this invention —is to allow the clinician or anesthesiologist to mount receptors quickly at the desired sites without the need to prepare the sites prior to attachment of the receptors, even where the patient has a significant amount of hair. The set up time for the clinician or anesthesiologist will be significantly reduced because the appliance automatically positions all seven receptors although the clinician need only locate three anatomically-precise mounting sites. The appliance is lightweight, flexible, adjusts to any head size, lays flat against the head, attaches with peel-and-stick adhesives, and does not require preparation of the sites before receptors are mounted.

The appliance also will allow the receptors to be positioned freely, without encumbrance, until the correct sites have been located, and is capable of holding the receptors in the desired positions and maintaining strong electrical contact with the patient even where the appliance is subjected to significant head movement. The appliance further adapts to the human head regardless of its shape and size and does not require manual size adjustments. The appliance does not put excessive pressure on the patient's head. It will hold the receptors in position for monitoring sessions lasting up to eight hours, even while being subjected to a reasonably foreseeable amount of movement of the patient's head. The appliance is designed so that receptors will not become dislodged which would interrupt transmission of electrical signals. The preferred embodiment includes embedded circuitry, which requires no separate wiring activity by the clinician.

The small number of receptors and the relatively modest size and weight of the appliance reduce the chance that the appliance would need to be removed during surgery to improve access to the patient. Leads from each of the receptors run to a quick-connect plug on the appliance that mates with the patient interface cable running to the monitoring console. This allows the monitoring console to be positioned in a convenient location where it will not interfere with ongoing surgical activities. The quick connect plug is positioned so that the patient interface cable will be unlikely to interfere with access to the patient's facial region.

The present invention is inexpensive to manufacture and is compatible for use as a medical disposable. This will ensure that the level of sanitation is consistent with use in a surgical environment. It will further assure that the expense, time, and risks associated with cleaning an appliance that will be used repeatedly are avoided and that the efficacy of the appliance is not compromised through repeated use.

BRIEF DESCRIPTION OF THE DRAWINGS

FIG. 4 is a detail showing the reservoir electrode.

DESCRIPTION OF THE PREFERRED EMBODIMENT

Figure 1:
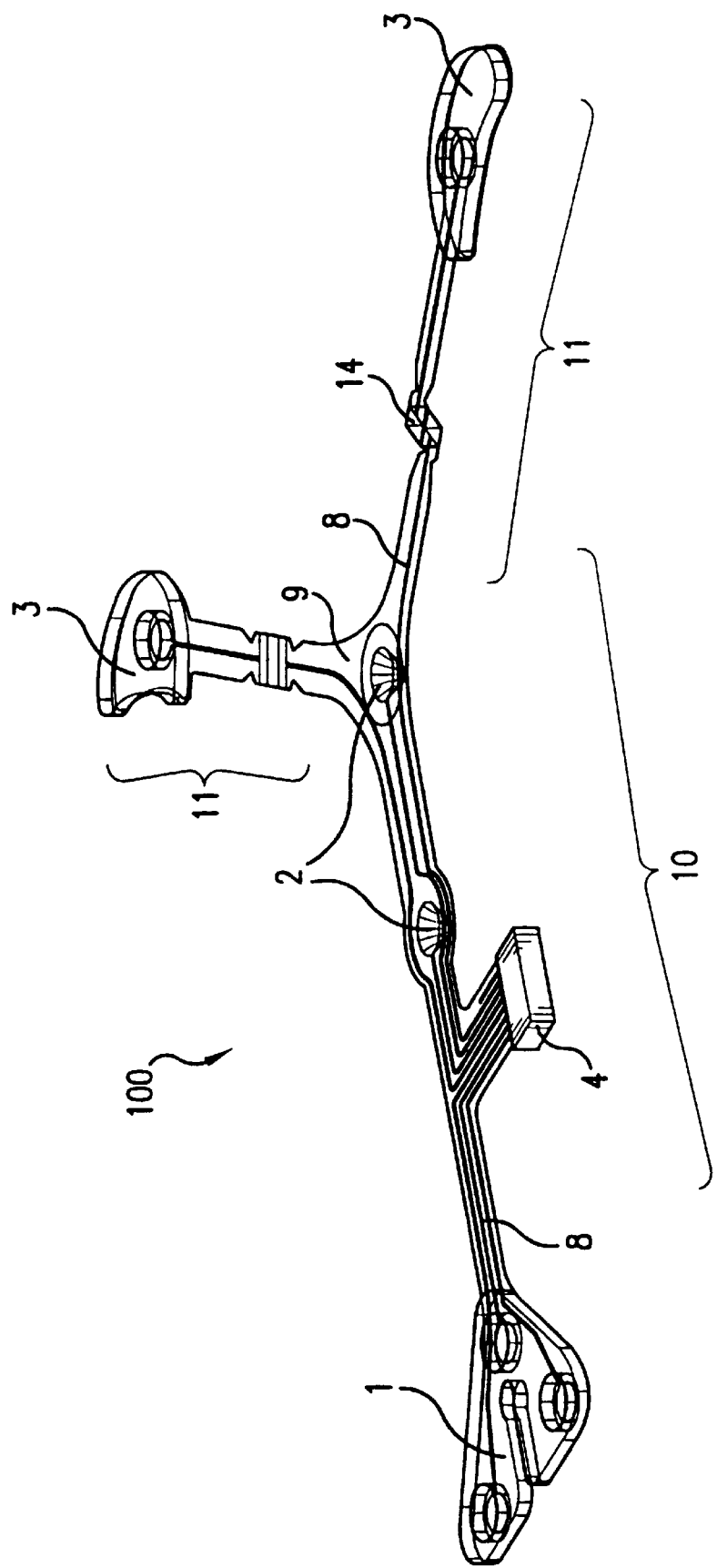
FIG. 1 portrays an isometric view of the appliance in a preferred embodiment.
Figure 2:
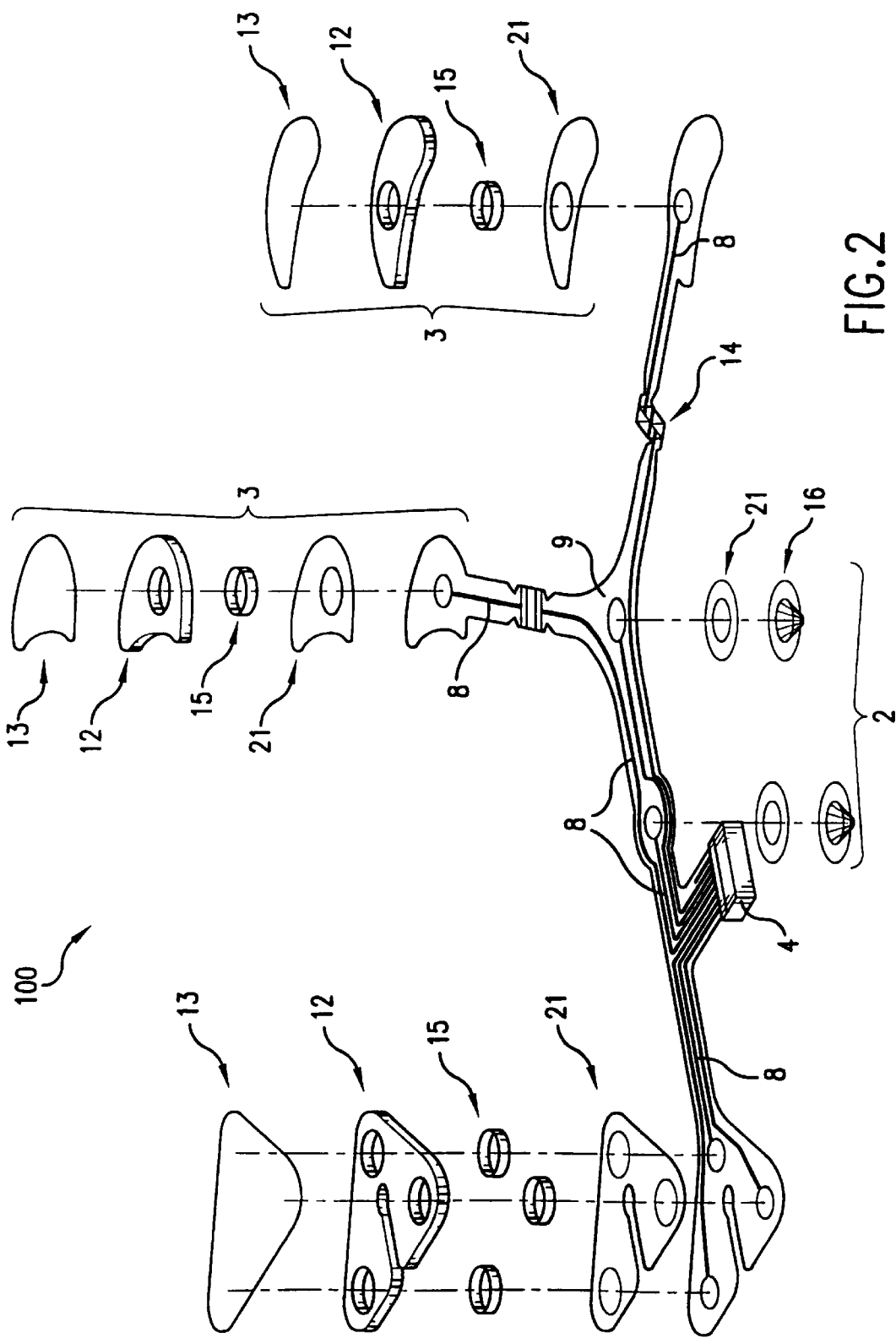
FIG. 2 sets forth an exploded isometric view of the appliance in a preferred embodiment.

FIG. 1 shows the assembled structure of self-adjusting headgear appliance 100 and FIG. 2 shows an exploded view of appliance 100. In this embodiment, the appliance comprises seven receptors: three frontal receptors 1, two central receptors 2 and two mastoid receptors 3 (one mastoid receptor being mounted behind each of the patient's ears). In the preferred embodiment, the receptors are positioned on the appliance so that, when secured on the patient's head, the frontal receptors 1 are mounted at sites Fp1, Fp2, FpZ', the central receptors 2 are mounted at sites CZ and PZ, and the mastoid receptors 3 are mounted at sites A1 and A2, where these alphanumeric designators correspond to predetermined anatomical positions defined by the International 10-20 system. In the preferred embodiment frontal receptors 1 and mastoid receptors 3 are gold- or silver-composition coated type receptors. Central receptors 2 consisting of gold- or silver-composition coated type electrodes are possible, as shown in FIGS. 1 and 2. However, in the preferred embodiment, the central receptors 2 are typically reservoir type electrodes, as described further below and shown in FIG. 4.

In the preferred embodiment, each frontal receptor 1, central receptor 2, and mastoid receptor 3 is affixed to strap 9. Strap 9 comprises a central section 10 and two mastoid sections 11, as shown in FIGS. 1 and 2. Strap may be comprised of polyethylene terephthalate ("PET") in the preferred embodiment, although other polymer sheet stock capable of carrying circuitry may be utilized.

As shown in FIGS. 1 and 2, each frontal receptor 1, central receptor 2, and mastoid receptor 3 has a distinct electrical connection to quick-connect plug 4. In the preferred embodiment, the distinct electrical connection between each receptor and quick-connect plug 4 is provided by a circuit 8 inked on strap 9. Alternatively, this electrical connection may be provided by metallic wire or ribbon (not shown) of a type and size compatible with the amount of electrical current flowing and the resistance inherent in the selected material. Quick-connect plug 4 is a multi-pin connector that corresponds matingly with a quick-connect plug on the patient interface cable hooking to the monitoring console (not shown).

In the preferred embodiment, frontal receptors 1 and mastoid receptors 3 are secured to the patient's head using adhesive patches 12, as shown in FIGS. 1 and 2. The three frontal receptors 1 are held by a single adhesive foam patch 12, as shown in FIGS. 1 and 2, which simplifies the task of positioning frontal receptors 1 at the desired sites Fp1, Fp2, and FpZ'. Adhesive foam patches 12 securing mastoid receptors 3 are of a modified half-moon shape to assist the clinician or anesthesiologist in placing these receptors at sites A1 and A2 behind the patient's ears.

The preferred embodiment uses adhesive patches 12 made from adhesive foam to secure frontal receptors 1 and mastoid receptors 3 to the patient. Alternatively, adhesive patches 12 may be constructed of any commonly-known flexible material and attached using any commonly-known biocompatible adhesive that allows adhesive patch 12 to mold to the contours of the patient's head at the intended attachment sites but is of a sufficiently rigid form to maintain the receptor flat against the patient's head in its corresponding anatomically-precise site for durations of up to eight hours while preventing twisting, creeping or separation. The sticky surface of each adhesive patch 12 is sealed with a release liner 13 which is removed before mounting the receptor at the appropriate site.

Figure 3:
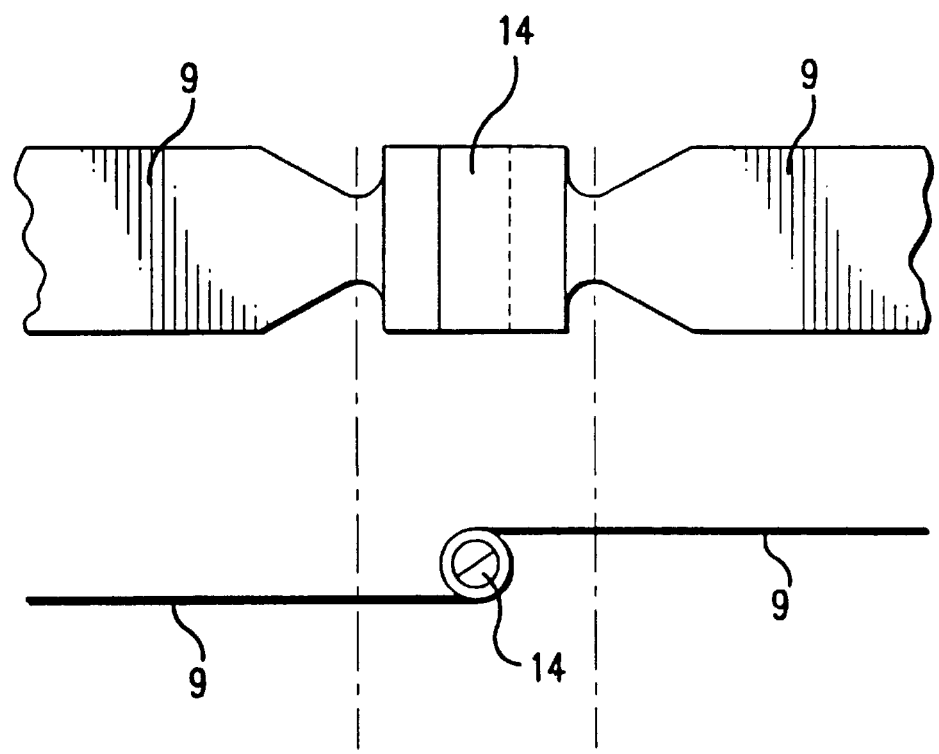
FIG. 3 is a detail showing the self-adjusting elastic coil used in the preferred embodiment.

In the preferred embodiment, adjustment of the appliance to accommodate different head shapes and sizes is provided by self-adjusting elastic coils 14 located on the mastoid sections 11 of strap 9, as shown in FIGS. 1 and 2. FIG. 3 shows front and side views of a typical self-adjusting elastic coil 14. Self-adjusting elastic coils 14 are formed integrally on mastoid sections 11 of strap 9. The self adjusting elastic coils 14 may be fabricated using thermoforming or cold forming manufacturing techniques. A portion of strap 9 is woundtightly to form this embodiment such that it acquires a permanent "set" in its coiled configuration. The mechanical properties of the material allow self adjusting Strap 14 to behave in an elastic manner when a tension force is applied to pull the coil open. Since self-adjusting elastic coil 14 is a continuous coil with no creases, an electrical circuit (conductive circuit) will maintain continuity through the coiled section. The elastic coil generates tension, takes up slack, and maintains excess material in a relatively small, confined area. The self-adjusting, constant tension characteristic of the coil ensures that the appliance will fit snugly on and nearly flush to the patient's head. This reduces the possibility that anything will be caught on the appliance during a surgical procedure or during invasive procedures such as intubation.

Self-adjusting elastic coil 14 is integral with both the primary structural component of the appliance and the media used for current/signal transmission (conductive circuit 3), and functions simultaneously as the elastic member in the appliance. Alternatively, self-adjusting elastic performance may be achieved by attaching rubber bands (not shown) in notches (also not shown) formed in the sides of the strap 9 adjacent to the coil when rolled up. By forming self-adjusting elastic coils 14 integrally with strap 9, the invention is simplified by reducing the number of components required to achieve the required functionality and performance. This simplicity reduces manufacturing costs and makes the appliance much easier for the clinician to use. Other traditional means of adjusting the length of the mastoid sections 11 of strap 9 are possible, such as elastic inserts, but are much less desirable because wires or other means for carrying the electrical current or signal become separate components complicating manufacturing and use while increasing cost of the appliance.

In the preferred embodiment, electrical contact with the patient is maintained by a conductive, electrolytic gel. As shown in FIG. 2, gel 22 is retained in frontal receptor 1 and mastoid receptor 3 locations by an open-cell sponge 15. FIGS. 1 and 2 show central receptor locations utilizing typically hemispherical reservoirs 16 with pressure openable slit flat surfaces on the side adjacent to the patient for holding gel 22 in the two scalp positions (serviced by central receptors 2). Pressing on the reservoir will deploy the gel to make contact with the patient's skin. An embodiment employing braille tip electrodes 17 in FIG. 4 is preferred because it may enhance performance of central receptors 2 which must operate in an environment where hair is typically present.

Braille tip electrodes 17 in FIG. 4 use a conductive sensor element that has protuberances 18 molded into it. Protuberances 18 enable braille tip electrodes 17 to reach the skin through the hair follicles. Since protuberances 18 are conductive, braille tip electrodes 17 allow deployment of the sensor surface through the hair to the skin. Braille tip electrodes 17 have perforations 20 that enable conductive gel to be deployed from attached reservoir 16 through the hair onto the skin. Reservoir 16 holds a substantial volume of conductive gel 22 which allows braille tip electrode 17 to wet out the hair follicles and skin in the area between the skin and protuberances 18, thereby ensuring adequate signal quality.

Adhesive patches 12, open cell sponges 15, and reservoirs 16 shown in FIG. 2, and reservoirs 16 shown with braille tip electrodes 17 shown in FIG. 4, are secured to strap 9 using adhesive 21.

The appliance is attached to the patient's head quickly and easily. The clinician would first locate FpZ'and mount frontal receptors 1 by removing release liner 13 from adhesive patch 12. The clinician would next locate A1 and A2 and mount mastoid receptors 3 by removing release liners 13 from each moon-shaped adhesive patch 12. Central receptors 2 would be positioned automatically through action of the self-adjusting elastic coils 14. The clinician would then press reservoirs 16 to eject connective gel onto the patient's scalp. To complete the set up, electrical connection to the monitoring unit would be effected by snapping the patient interface cable into quick connect plug 4.

We claim:

1. An appliance for collecting electroencephalographic signals from a patient's head, comprising:
   a. a flexible strap consisting of an anterior segment which is adapted to traverse longitudinally the crown of said patient's head and a plurality of posterior branch segments, each posterior branch segment projecting from the posterior end of the anterior segment at an angle to the center line of the anterior segment and being adapted to traverse therefrom portions of the rear of the patient's head, and each of the plurality of posterior branch segments incorporating a means for adjustment of length of said posterior branch segment,
      (1) each of the plurality of posterior branch segments extending from the posterior end of said anterior segment to an adhesive patch on which at least one receptor is mounted,
      (2) two of the plurality of posterior branch segments being adapted to be disposed symmetrically on either side of the patient's head so as to comprise two mastoid segments,
      (3) each of the at least one receptor on the adhesive patch of each of two mastoid segments comprising a mastoid receptor adapted to be placed in a predetermined anatomical position behind each of the patient's ears in the mastoid region;
   b. at the anterior end of said anterior segment, a frontal adhesive patch in which is mounted at least one receptor situated so that the at least one receptor may be placed in at least one predetermined anatomical position on the forehead of said patient;
   c. in the central and posterior portions of the anterior segment, at least one crown receptor mounted so that it may be placed in at least one predetermined anatomical position on the crown of the patient's head,
   d. a connector tab extending from said anterior segment to a connector; and
   e. electrical conductors contained in said strap so as to connect electrically each of the at least one receptor in the frontal adhesive patch, the at least one crown receptor, the mastoid receptors, and any other receptor with a corresponding contact in the connector so that independent signals may be transmitted from each receptor out of the appliance to external devices.

2. The appliance of claim 1 in which the plurality of posterior branch segments comprise exactly two posterior branch segments projecting substantially symmetrically so that the anterior segment and the exactly two posterior branch segments collectively form the general shape of a Y.

3. The appliance of claim 2 wherein the total number of receptors is 7.

4. The appliance of claim 2 wherein the total number of receptors is 5.

5. The appliance of claim 1 in which said plurality of posterior branch segments comprise exactly two mastoid segments and wherein said frontal adhesive patch contains exactly three receptors mounted in predetermined anatomical positions, said central and posterior portions of the anterior segment contain exactly two crown receptors in predetermined anatomical positions, and said adhesive patches attached to said exactly two mastoid segments each contains exactly one mastoid receptor.

6. The appliance of claim 5 wherein said exactly three receptors in said frontal adhesive patch are adapted to be located at sites Fp1, Fp2, FpZ', where these alphanumeric designators correspond to predetermined anatomical positions defined by the International 10-20 system.

7. The appliance of claim 5 wherein said exactly two crown receptors are adapted to be located at sites CZ and PZ, where these alphanumeric designators correspond to predetermined anatomical positions defined by the International 10-20 system.

8. The appliance of claim 5 wherein said exactly one mastoid receptor in each of said mastoid segments is adapted to be located respectively at sites A1 and A2 on the two sides of the patient's head, where these alphanumeric designators correspond to predetermined anatomical positions defined by the International 10-20 system.

9. The appliance of claim 1 wherein said means for adjustment of the length of each of said at least two posterior branch segments consists of self-adjusting elastic coils between the posterior end of the anterior segment and the adhesive patch attached to the posterior branch segment.

10. The appliance of claim 9 wherein each of said self-adjusting elastic coils comprises a rollup clip formed by having a portion of said segment wrapped around a spring-loaded central hub in such a way that the tension exerted by said spring-loaded central hub causes a portion of said segment to roll up upon itself and such that the portion of said segment not rolled up lies flat against the patient's head.

11. An appliance for mounting on the head of a patient for collecting electroencephalographic signals, comprising:
   a. a frontal adhesive patch incorporating a plurality of receptors adapted to being secured in predetermined anatomical positions on the forehead of said patient;
   b. a central strap extending from said frontal adhesive patch adapted to traverse longitudinally the crown of the patient's head, said central strap incorporating a means for adjustment of length and incorporating at least one receptor located so as to be adapted to being mounted in at least one predetermined anatomical position on the crown of patient's head;
   c. a circumferential band adapted to pass about the patient's head above the patient's ears and attached to said frontal adhesive patch;
   d. two mastoid straps extending downward from said circumferential band to two mastoid adhesive patches each incorporating a means for adjustment of length, each mastoid adhesive patch incorporating at least one receptor situated so as to be secured by the adhesive patch in a predetermined anatomical position on the patient, one of said mastoid adhesive patches being adapted to having the at least one receptor secured to a predetermined anatomical position behind the left ear of the patient and the other of said mastoid adhesive patches being adapted to having the at least one receptor secured to a predetermined anatomical position behind the right ear of the patient;

e said plurality of receptors adapted to being secured in predetermined anatomical positions comprising three frontal receptors, two central receptors, and two mastoid receptors.

12. The appliance of claim 11 wherein said frontal receptors are adapted to being located at sites Fp1, Fp2, FpZ'on the patient's head where these alphanumeric designators correspond to predetermined anatomical positions defined by the International 10-20 system.

13. The appliance of claim 11 wherein said central receptors are adapted to being located at sites CZ and PZ on the patient's head, where these alphanumeric designators correspond to predetermined anatomical positions defined by the international 10-20 system.

14. The appliance of claim 11 wherein said mastoid receptors are adapted to being located at sites A1 and A2 on the patient's head, where these alphanumeric designators correspond to predetermined anatomical positions defined by the international 10-20 system.

15. The appliance of claim 11 wherein said means for adjustment of length of said central strap and said mastoid strap comprises a rollup clip comprising a portion of said central strap and said mastoid strap respectively wrapped around a spring-loaded central hub in such a way that the tension exerted by said spring-loaded central hub causes a portion of said central strap and said mastoid strap respectively to roll up upon itself and such that the portion of said central strap and said mastoid strap respectively not rolled up lies flat against the patient's head.

* * * * *